US012611119B2

(12) United States Patent
Just et al.

(10) Patent No.: US 12,611,119 B2
(45) Date of Patent: *Apr. 28, 2026

(54) TEST METHOD FOR ASSESSING SPINAL OR SKELETAL ALIGNMENT

(71) Applicant: Madad Pty Ltd, Wacol (AU)

(72) Inventors: Morrison Just, Wacol (AU); Daniel Green, Wacol (AU)

(73) Assignee: Madad Pty Ltd (AU)

( * ) Notice: Subject to any disclaimer, the term of this patent is extended or adjusted under 35 U.S.C. 154(b) by 341 days.

This patent is subject to a terminal disclaimer.

(21) Appl. No.: 18/554,333

(22) PCT Filed: Apr. 14, 2022

(86) PCT No.: PCT/AU2022/050338
§ 371 (c)(1),
(2) Date: Oct. 6, 2023

(87) PCT Pub. No.: WO2022/217318
PCT Pub. Date: Oct. 20, 2022

(65) Prior Publication Data
US 2024/0350031 A1     Oct. 24, 2024

(30) Foreign Application Priority Data

Apr. 14, 2021     (AU) ................................. 2021901098

(51) Int. Cl.
*A61B 5/107*          (2006.01)
*A47C 31/12*          (2006.01)
(Continued)

(52) U.S. Cl.
CPC .......... *A61B 5/1077* (2013.01); *A47C 31/123* (2013.01); *A61B 5/1071* (2013.01); *A61B 5/742* (2013.01); *G09B 23/32* (2013.01)

(58) Field of Classification Search
CPC ..... A61B 5/1077; A61B 5/1071; A61B 5/742; A47C 31/123; G09B 23/32; G01B 5/207
See application file for complete search history.

(56) References Cited

U.S. PATENT DOCUMENTS

| | | | |
|---|---|---|---|
| 4,669,302 A | 6/1987 | Wagner et al. | |
| 2019/0021929 A1 | 1/2019 | Einav et al. | |
| 2023/0233104 A1* | 7/2023 | Caviedes | ............. A61B 5/4561 |
| | | | 600/595 |

FOREIGN PATENT DOCUMENTS

| | | | |
|---|---|---|---|
| CN | 103169477 | | 6/2013 |
| CN | 104799613 | | 7/2015 |
| CN | 212141374 U | * | 12/2020 |

* cited by examiner

*Primary Examiner* — Stephen D Meier
*Assistant Examiner* — Quang X Nguyen
(74) *Attorney, Agent, or Firm* — Dureska & Moore, LLC; David P. Dureska; Benjamin J. Chojnacki

(57)                ABSTRACT

A method for measuring a profile of a manikin. The method comprises the steps of: suspending the manikin by a suspension frame, connecting one or more measuring devices to the manikin at one or more measuring points, raising a support surface to meet the manikin, supporting the manikin by the support surface, and measuring by the one or more measuring devices, differences in angles of the manikin profile between the suspended configuration of the manikin and the supported configuration of the manikin. The manikin comprises one or more articulating joints defining a manikin profile. The manikin also defines a suspended configuration when suspended by the suspension frame, and a supported configuration when supported by the support surface. The method provides a process to replicate and measure human physiology when engaged with a surface.

20 Claims, 6 Drawing Sheets

(51) Int. Cl.
    *A61B 5/00*         (2006.01)
    *G09B 23/32*      (2006.01)

100

140

135

120

120

115

125

130

110

105

110

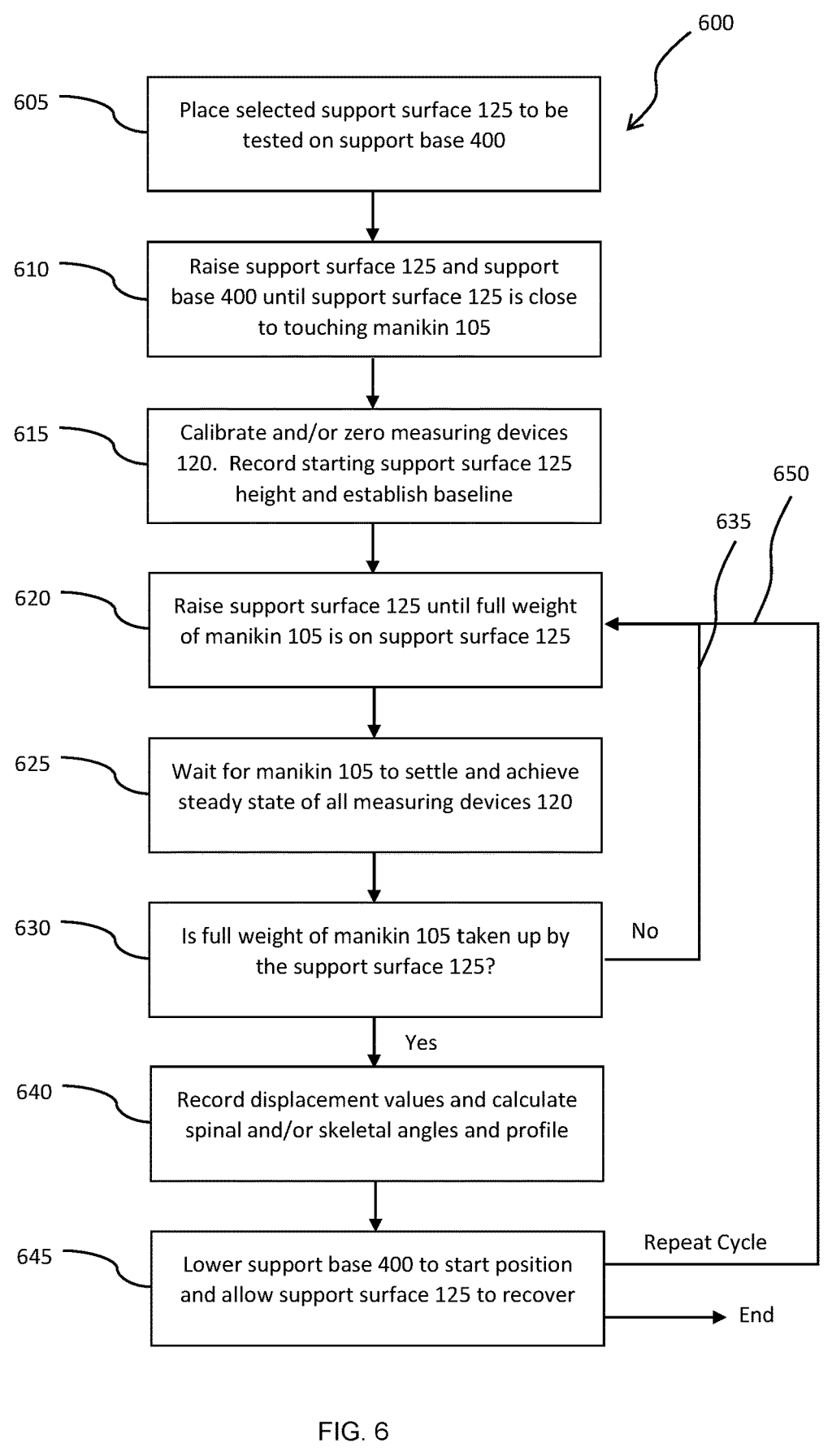

600

605 — Place selected support surface 125 to be tested on support base 400

610 — Raise support surface 125 and support base 400 until support surface 125 is close to touching manikin 105

615 — Calibrate and/or zero measuring devices 120. Record starting support surface 125 height and establish baseline 620 — Raise support surface 125 until full weight of manikin 105 is on support surface 125

625 — Wait for manikin 105 to settle and achieve steady state of all measuring devices 120

630 — Is full weight of manikin 105 taken up by the support surface 125?

No

635

650

Yes

640 — Record displacement values and calculate spinal and/or skeletal angles and profile 645 — Lower support base 400 to start position and allow support surface 125 to recover Repeat Cycle End

FIG. 6

TEST METHOD FOR ASSESSING SPINAL OR SKELETAL ALIGNMENT

This application claims the benefit of International Application No. PCT/AU2022/050338, filed Apr. 14, 2022, which claims the benefit of Australian Patent Application No. 2021901098, filed Apr. 14, 2021.

FIELD OF THE INVENTION

The present invention relates to a method for measuring spinal or skeletal angles. In particular, although not exclusively, the invention relates to a method for measuring spinal or skeletal angles of a manikin representing the human form.

BACKGROUND TO THE INVENTION

Numerous types of human test apparatuses and methods are commonly used to determine usability, ergonomics, and safety. Typically, a manikin is used to simulate the effects of a human body's interaction with a product, or the effects of an environmental situation on the human body.

An example is the apparatus disclosed by U.S. Pat. No. 4,669,302, titled 'Deflection and topography assessment mechanism anthropomorphically natural', wherein a manikin is used to depress a surface such as a mattress, allowing analysis of a resulting mattress contour. Tests such as these generally focus exclusively on the supine, i.e. back sleeping position, and provide limited data on human physiology as, primarily, the motivation is to analyse a mattress contour formed by the weighted manikin. These methods also generally lower a manikin onto a mattress in order to evaluate the contours and depressions caused by the manikin.

Other systems such as that disclosed by U.S. Pat. No. 5,628,230, titled 'Method and apparatus for testing the efficacy of patient support systems', disclose anthropomorphic models for measuring pressure distribution over an anthropomorphic manikin, primarily for the purpose of analysing the likelihood of pressure related complications such as decubitus ulcers and similar conditions.

There is therefore a need for an improved method for measuring a manikin on a support surface, in particular for a method for measuring spinal and/or skeletal angles of a manikin lying in a supine (back) or lateral (side) position.

OBJECT OF THE INVENTION

It is a preferred object of the invention to provide methods and/or apparatuses and/or systems that address or ameliorate one or more of the aforementioned problems of the prior art and/or provide a useful commercial alternative.

SUMMARY OF THE INVENTION

In one form, although not necessarily the broadest form, the invention resides in a method for measuring a profile of a manikin, the method comprising the steps of: suspending the manikin by a suspension frame, the manikin comprising one or more articulating joints defining a manikin profile, wherein the manikin defines a suspended configuration when suspended by the suspension frame; connecting one or more measuring devices to the manikin at one or more measuring points; raising a support surface to meet the manikin, supporting the manikin by the support surface, wherein the manikin defines a supported configuration when supported by the support surface; and measuring by the one or more measuring devices, differences in angles of the manikin profile between the suspended configuration of the manikin and the supported configuration of the manikin.

Preferably, the method further comprising the step of positioning the manikin in a supine position or a lateral position.

Preferably, the method further comprises the step of adjusting resistance and/or angle of articulation in the articulating joints.

Preferably, the manikin profile in the suspended configuration is sagittal to the manikin.

Preferably, the manikin comprises an articulating hip joint that hinges and rotates.

Preferably, the method further comprises the step of suspending the manikin on the suspension frame via a plurality of cords.

Further preferably, the plurality of cords are tight when in the suspended configuration, and the plurality of cords are slack when in the supported configuration.

Preferably, the full weight of the manikin is on the suspension frame when in the suspended configuration, and the full weight of the manikin is on the support surface when in the supported configuration.

Preferably, the support surface is a mattress.

Preferably, the method further includes the step of supporting a head of the manikin by a counterweight and maintaining the head in a neutral position along the manikin profile.

Preferably, the method further includes the step of attaching the one or more measuring points along the manikin profile.

Preferably, the method further includes the step of mounting the measuring devices on the suspension frame and connecting the measuring devices to the manikin at the one or more measuring points, wherein the measuring devices are electronic devices.

Preferably, the method further includes the step of calibrating the measuring devices.

Preferably, the method further includes the step of controlling raising and lowering of the support surface via a control interface.

Preferably, the method further includes the step of the control interface processing, displaying, and/or outputting data from the one or more measurement devices.

Preferably, the method further includes including the step of sizing the manikin according to a size between a 99th percentile male and a 1st percentile female.

Preferably, the method further includes the step of weighting the manikin according to a size between a 99th percentile male and a 1st percentile female.

Preferably, differences in angles measured by the one or more measuring devices is calculated from differences in vertical height.

Preferably, the method further includes the step of assessing the changes in angles of the manikin profile against a set of acceptable limits.

Preferably, the method further includes the step of determining an average of differences in angles of the manikin profile over repeated cycles of the method.

BRIEF DESCRIPTION OF THE DRAWINGS

To assist in understanding the invention and to enable a person skilled in the art to put the invention into practical effect, a preferred embodiment of the invention will be described by way of example only with reference to the accompanying drawings, in which:

FIG. 6 is a flowchart illustrating a method of use for the system of FIG. 1.

DETAILED DESCRIPTION OF THE INVENTION

Figure 1:
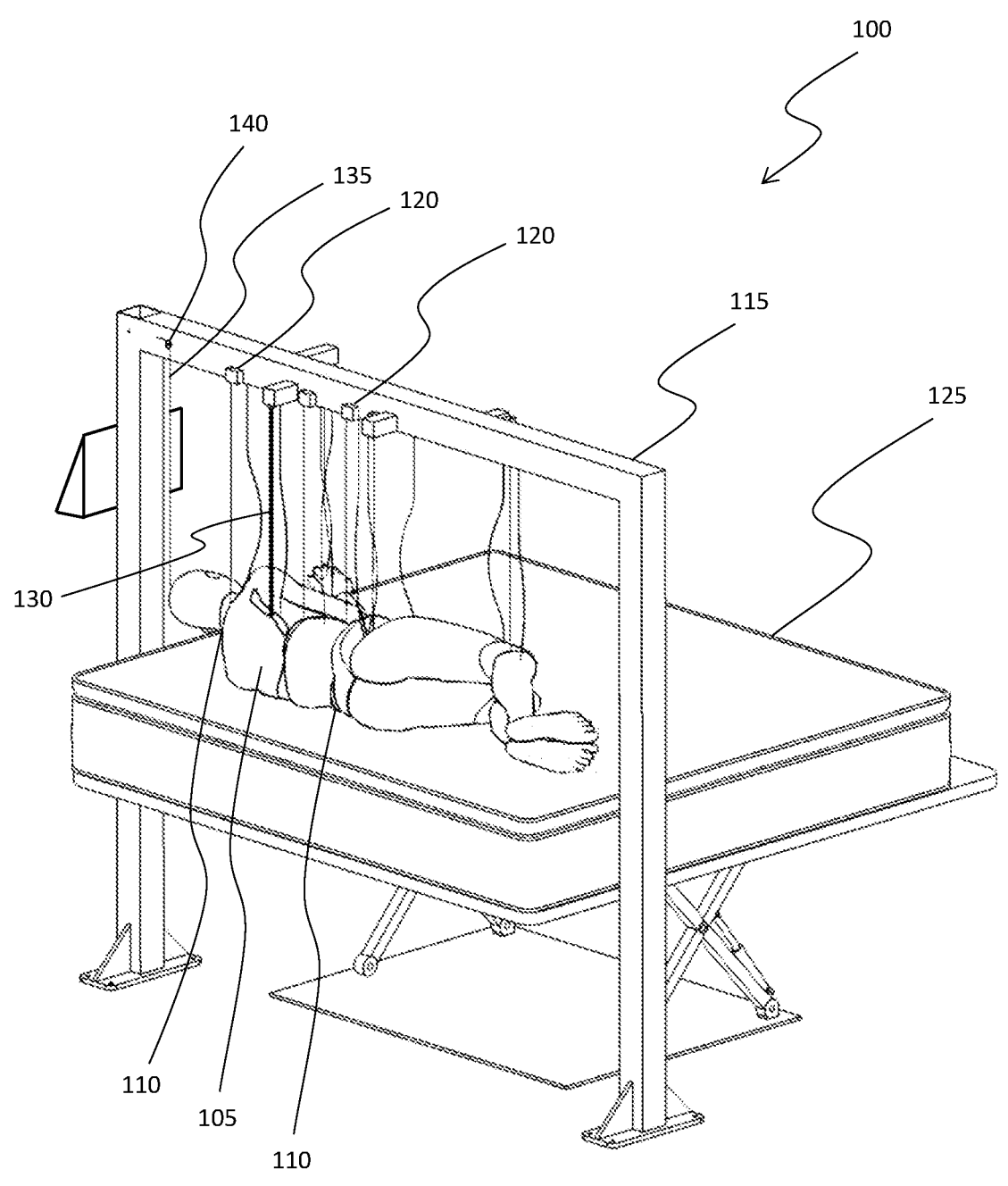
FIG. 1 is a perspective view of a system for measuring spinal or skeletal angles, with a manikin in a supported configuration.

The present invention relates to a method for measuring spinal or skeletal angles. However, it will be appreciated that embodiments of the present invention can apply to other forms of manikin testing methods. Elements of the invention are illustrated in concise outline form in the drawings, showing only those specific details that are necessary to understanding the embodiments of the present invention, but so as not to clutter the disclosure with excessive detail that will be obvious to those of ordinary skill in the art in light of the present description.

According to one aspect, the present invention is defined as a method for measuring spinal or skeletal angles of a manikin, the method comprising the steps of: suspending the manikin by a suspension frame, the manikin comprising one or more articulating joints defining a manikin profile, wherein the manikin defines a suspended configuration when suspended by the suspension frame; connecting one or more measuring devices to the manikin at one or more measuring points; raising a support surface to meet the manikin, supporting the manikin by the support surface, wherein the manikin defines a supported configuration when supported by the support surface; and measuring by the one or more measuring devices, differences in angles of the manikin profile between the suspended configuration of the manikin and the supported configuration of the manikin.

Advantages of some embodiments of the present invention include the ability to measure changes to the spinal and/or skeletal profile in both supine and lateral positions. By suspending the manikin in the supine or lateral position, and raising a support surface to meet the manikin, the present system is able to easily establish a neutral spinal and/or skeletal profile and efficiently analyse the predicted spinal and/or skeletal profile of a person lying on his or her back or side on the support surface. By implementing articulating joints, the manikin is also able to more closely imitate the sleeping position and movement of a human being when settling into a support surface such as a mattress. Measuring devices connected to the manikin are able to record any changes to the spinal and/or skeletal profile caused by interaction with the support surface, providing data on any height and angular deviation or changes of the spinal and/or skeletal profile. The present invention therefore assists in data gathering and measurement of sleep physiology, with particular emphasis on skeletal and spinal and/or skeletal angles in a sleeping position.

Those skilled in the art will appreciate that not all of the above advantages are necessarily included in all embodiments of the present invention.

FIG. 1 is a perspective view of a system 100 for measuring spinal and/or skeletal angles, with a manikin in a supported configuration. In one form, although not necessarily the broadest form, the invention resides in a method for measuring spinal and/or skeletal angles of a manikin 105, the method comprising the steps of: suspending a manikin 105 by a suspension frame 115, the manikin 105 comprising one or more articulating joints 110 and a spinal and/or skeletal profile defining a manikin profile, wherein the manikin 105 defines a suspended configuration when suspended by the suspension frame 115; connecting one or more measuring devices 120 to the manikin 105 at one or more measuring points; raising a support surface 125 to meet the manikin 105, the support surface 125 adjustable in at least a vertical axis, supporting the manikin 105 by the support surface 125, wherein the manikin 105 defines a supported configuration when supported by the support surface 125; and measuring by the one or more measuring devices 120, differences in spinal and/or skeletal angles of the manikin profile between the suspended configuration of the manikin 105 and the supported configuration of the manikin 105.

In a preferred embodiment, the method further comprises the step of adjusting resistance and/or angle of articulation in the articulating joints 110. This allows the manikin 105 to be adjusted and closely imitate the pose and response of a human being as the manikin 105 settles onto the support surface 125. Further preferably, the support surface 125 is a mattress. The person skilled in the art will understand that the manikin 105 may gradually settle over time, depending on the firmness of the support surface 125 or mattress.

In a preferred embodiment, the method further comprises the step of positioning the manikin 105 in a supine position or a lateral position, to replicate a particular lying position of human subjects. As mentioned, the adjustable articulating joints 110 allow the manikin 105 to be fine-tuned to achieve desired angles when lying on the support surface 125. Optionally, these adjustments may be made through internal springs that are adjustable to increase or decrease resistance. The desired angles and limitations may be established through ergonomic data collection or according to medical research. Preferably, the articulating joint 110 at the hip of the manikin 105 replicates human movement parameters by providing limit and tension adjustable joints that both hinge and rotate. By allowing the hips of the manikin 105 to hinge sideways and also rotate, the knees of the manikin 105 are able to rest properly on the support surface 125 and closely replicate the natural flex and rotation of the human body when in a supine position or a lateral position. The person skilled in the art will also understand that limitations on the desired angles may be imposed on the articulating joints 110 to simulate flexibility and movement ranges of the human body, including restrictions where necessary, such as in the context of rehabilitation.

Optionally, when the manikin 105 is positioned in the lateral position, the manikin 105, comprising a torso, can be attached to the suspension frame 115 via a vertical stabiliser 130. The vertical stabiliser 130 retains the torso and effectively keeps the torso upright, so that the manikin 105 in the lateral position is maintained in a position where the shoulders are vertically stacked. This allows the manikin 105 to replicate with greater accuracy the physical pose of a lateral lying human being and maintain reference to the suspension frame 115. With the vertical stabiliser 130 connecting the manikin 105 to the suspension frame 115, the manikin 105 is able to move along the vertical stabiliser vertically, horizontally, and rotationally on a coronal plane or a plane parallel to the vertical plane of the suspension frame 115. The person skilled in the art will understand that the vertical stabiliser 130 can also be implemented in the supine position as necessitated by situations where the torso, or other members of the manikin 105, require stabilisation to maintain desired postures and/or parameters.

Preferably, the method further includes the step of using a counterweighted cord 135 to support the head of the manikin 105, wherein the counterweighted cord 135 is fed through rollers 140 and into the body of the suspension frame 115.

Figure 2:
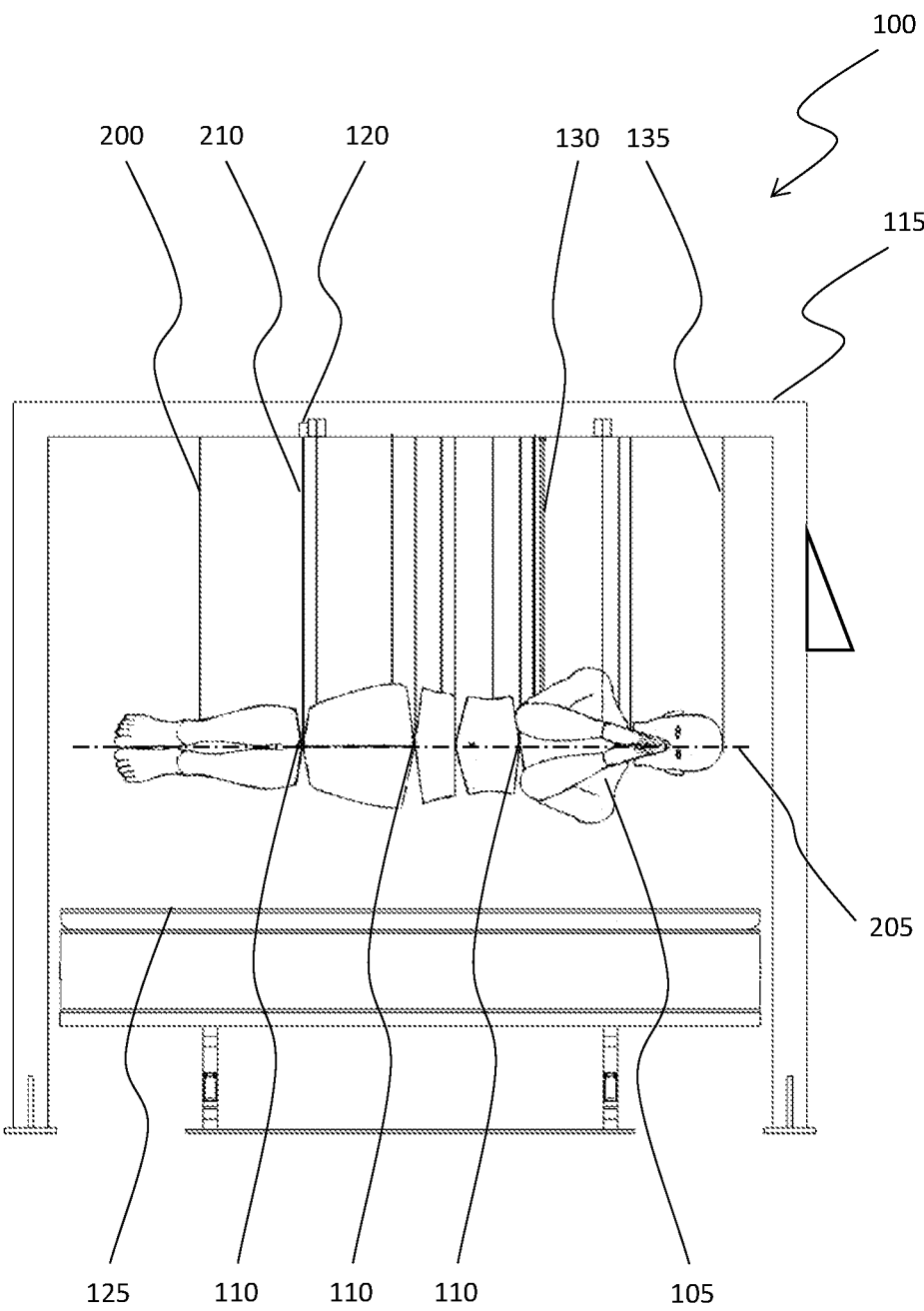
FIG. 2 is a side view of the system of FIG. 1 with a manikin in a suspended configuration.

FIG. 2 is a side view of the system of FIG. 1 with a manikin 105 in a suspended configuration. In a preferred embodiment, the method comprises the step of suspending the manikin 105 on the suspension frame 115 via a plurality of cords 200. In the suspended configuration, the plurality of cords 200 are tight and suspend the manikin 105 in a neutral position. With the manikin 105 attached to the suspension frame 115 via the plurality of cords 200, the full weight of the manikin is on the suspension frame 115 when in the suspended configuration.

In a preferred embodiment, the spinal and/or skeletal profile, defining the manikin profile, in the suspended configuration is sagittal to the manikin 105, representing a spine and/or skeletal profile running up and down the human body in a symmetrical and/or straight line. By way of reference, this is illustrated by a centre line 205. Preferably, the method includes the step of levelling and calibrating the suspended manikin 105 in the suspended configuration so that a neutral spinal and/or skeletal profile is established, and the spinal and/or skeletal profile is symmetrical and/or straight when viewed from the front of the manikin 105. Further preferably, the method includes the step of calibrating or zeroing the measuring devices 120 when the manikin 105 is in the suspended configuration.

Preferably, the method includes the step of connecting the measuring devices 120 to measuring points located along the spinal and/or skeletal profile of the manikin 105. Optionally, the measuring devices 120 can be configured to measure measuring points located along the spinal and/or skeletal profile of the manikin 105. The person skilled in the art will understand that measurement of particular measuring points will not necessarily require physical contact and direct attachment of the measuring devices 120 to the measuring points.

Further optionally, the method includes the step of arranging the measuring devices 120 so that the manikin profile is defined and/or limited by other physiological structures, with gathered measurement data correlating to muscular alignment and/or other anatomical structures such as tendons, joints, and connective tissue.

Preferably, the method includes the step of mounting the measuring devices 120 on the suspension frame 115 and then connecting the measuring devices 120 to the manikin 105 at the measuring points. The person skilled in the art will understand that the measuring devices 120 may be analogue or digital gauges calibrated to zero when the respective measuring point is on the established neutral spinal profile. In a preferred embodiment, the one or more measuring devices 120 are electronic devices. Further preferably, the measuring devices 120 are string potentiometers which draw in strings 210 under tension, thereby measuring the vertical movement and linear position of the measuring points. Pre-established distances between each measuring point running along the spinal and/or skeletal profile will allow changes in the spinal and/or skeletal profile between the suspended configuration and the supported configuration to be accurately measured and calculated, forming a complete and accurate representation of the spinal and/or skeletal profile defining the manikin profile.

Figure 3:
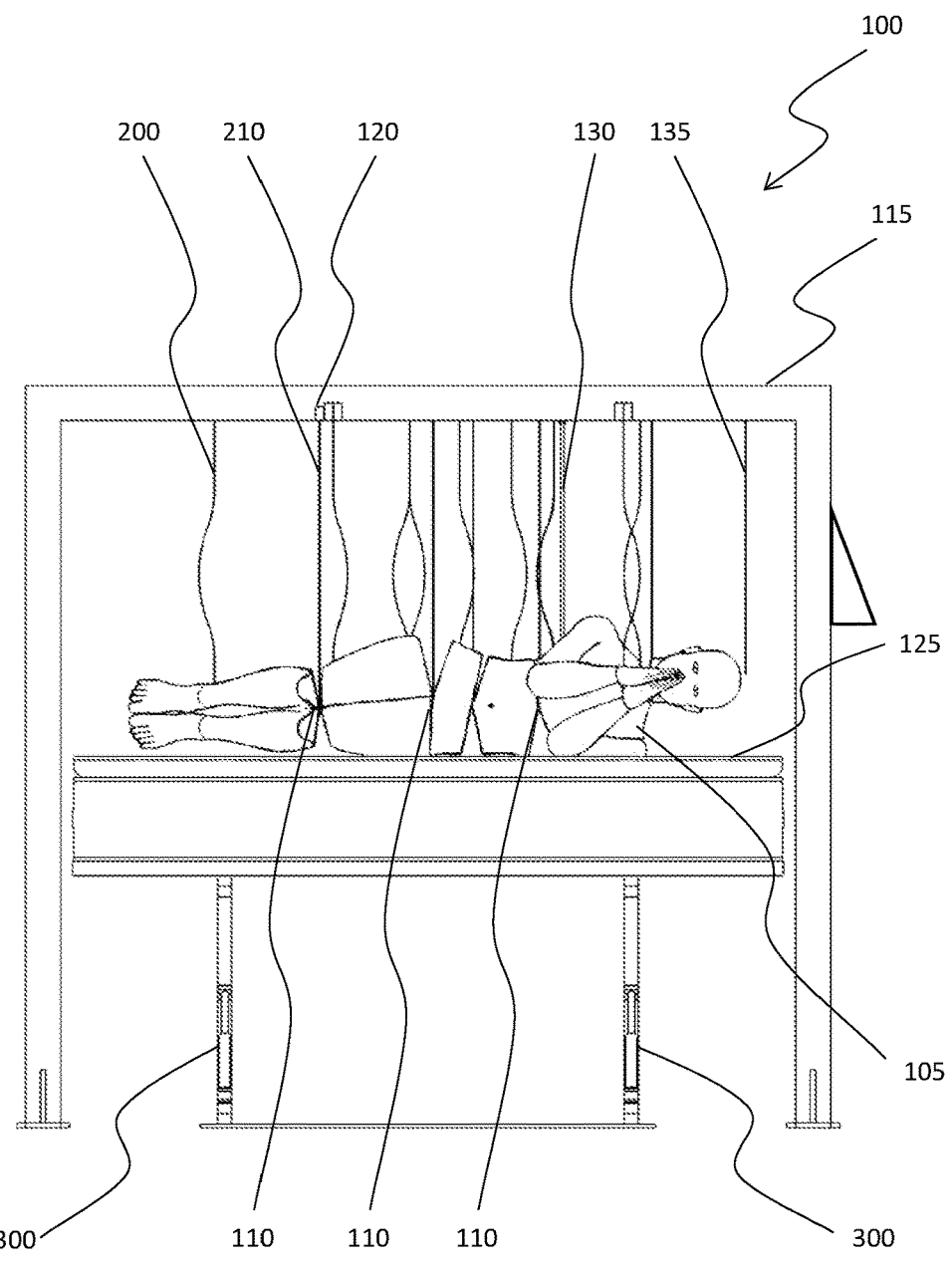
FIG. 3 is a side view of the system of FIG. 1 with the manikin in the supported configuration.

FIG. 3 is a side view of the system of FIG. 1 with the manikin in the supported configuration. In a preferred embodiment, the method includes the step of supporting the full weight of the manikin 105 on the support surface 125 when in the supported configuration. With the full weight of the manikin 105 resting on the support surface 125, the plurality of cords 200 become completely slack. As such, the plurality of cords 200 must be strong enough to suspend the manikin 105 and be supple enough so as to not influence or impact the measurement data. Though the plurality of cords 200 for suspending the manikin 105 become slack, the strings 210 of the one or more measuring devices 120 remain taught.

The plurality of cords 200 become slack after the full weight of the manikin 105 is supported by the support surface 125. However, an exception to this is the counterweighted cord 135 suspending the head of the manikin 105, wherein the counterweighted cord 135 remains taught and the head is maintained in a neutral position along the spinal profile even as the weight of the manikin 105 is taken up by the support surface 125. The counterweighted cord 135 independently supporting the head mimics the elevation of a pillow, mitigating any inadvertent distortion of the spinal profile caused by an unnaturally angled neck, and maintains the pose of a sleeping human using a pillow. Without the counterweighted cord 135 holding the head in a neutral position, the position and angle of an adjoining torso section may be influenced. To achieve balance, the counterweighted cord 135 may be routed over a series of rollers 140 (not shown) running the counterweighted cord 135 into the supporting frame 115 and down to an adjustable counterweight so that the head is consistently held in the neutral position along the spinal and/or skeletal profile defining the manikin profile.

In a preferred embodiment, the method includes the step of raising the support surface 125 in the vertical axis to support the manikin 105. The support surface 125 may be raised by one or more lifts 300 which may take on the form of pneumatic lift. As the one or more lifts 300 raises the support surface 125, the support surface is offered up from below to meet and engage the passively suspended manikin 105. The person skilled in the art will understand that various types of mechanical lifts may be used, along with levelling devices, as long as the support surface 125 is able to stably engage the suspended manikin 105.

Figure 4:
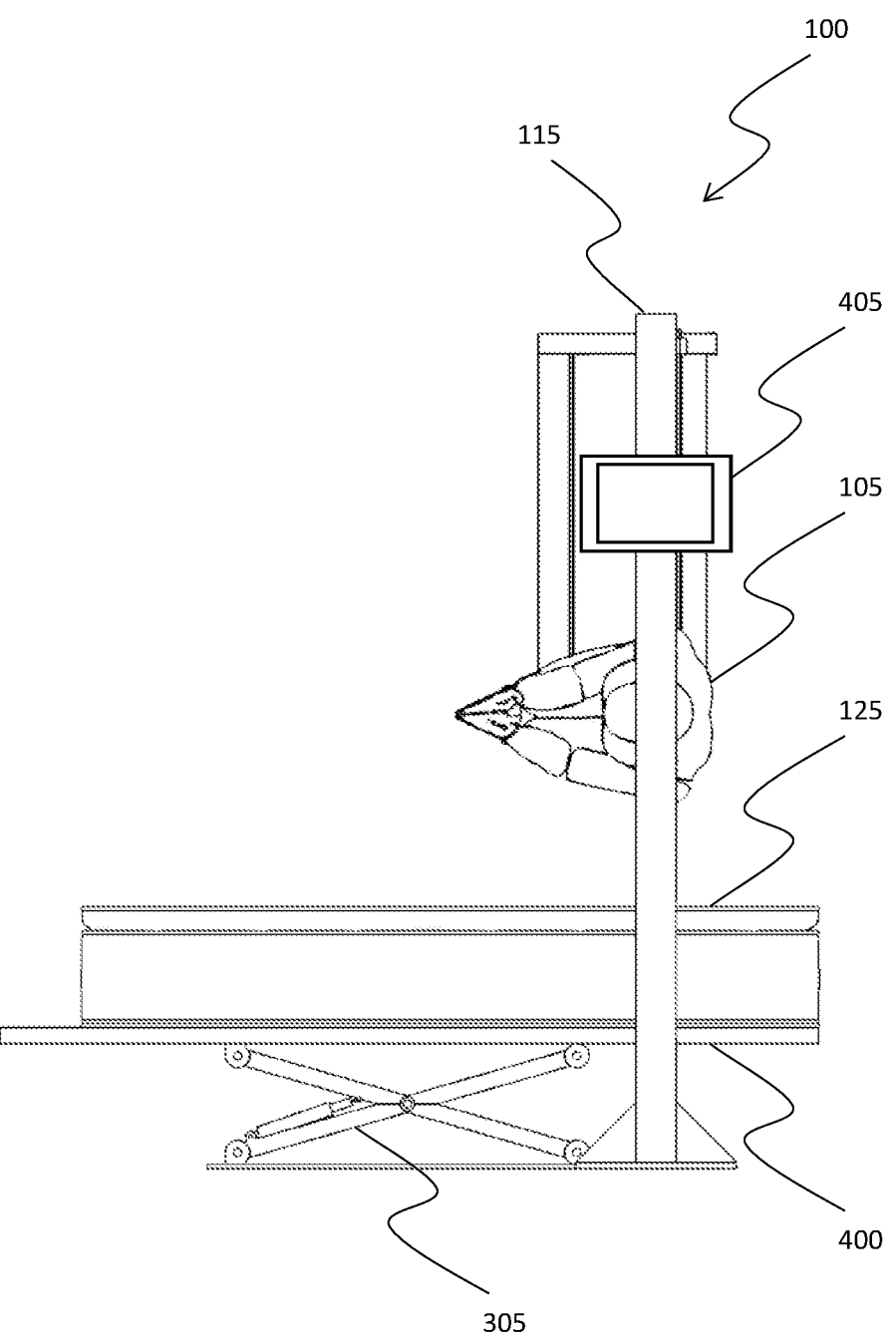
FIG. 4 is a further side view of FIG. 2.

FIG. 4 is further side view of FIG. 2, viewed down from the head of the manikin 105. In a preferred embodiment, the method includes the step of resting the support surface 125 on a support base 400 connected to the one or more lifts 300. This allows the support surface 125 to be easily and quickly changed out, to test different support surfaces 125 with different parameters, such as firmness. As the manikin 105 is passively suspended on the suspension frame 115, it is not necessary to make frequent changes to the manikin 105 or recalibration of the one or more measuring devices 120. Since the support surface 125 is the moving element, the manikin 105 and any previous calibration or alignment can remain constant. This greatly improves repeatability and consistency in the testing and data collection process.

Preferably, once the support surface 125 is raised to meet the passively suspended manikin 105, the one or more measuring devices 120 begins registering or recording any changes or differences in spinal and/or skeletal angles. Optionally, the changes or differences in angles is measured by the one or more measuring devices 120, calculated from differences in vertical height. As the manikin 105 becomes fully supported by the support surface 125, the measuring devices 120 located on the suspension frame 115 are able to determine a fully supported spinal and/or skeletal profile, as well as progressive changes in the one or more measuring points associated with each location on the spinal and/or skeletal profile. By converting the recorded measurement data into spinal and/or skeletal angles, a diagram or numerical measurements indicating the deviation of the spinal and/or skeletal profile from the centre line 205 is able to be established. A final measurement may be determined after the manikin 105 has stabilised on the support surface 125. As mentioned, some support surfaces such as thick mattresses may require a period of time for the weight of the manikin 105 to be fully settled into the mattress.

In a preferred embodiment, the method includes the step of recording changes and relative differences between the one or more measurement points, using the recorded information to calculate specific angles and/or measurements between sections of the manikin 105. The method can then include the step of assessing the angles and/or measurements against results from actual human subjects, or a range of acceptable limits established by medical professionals such as orthopaedic surgeons and other researchers. When the support surface 125 being tested is a mattress, these acceptable limits may indicate parameters which the measurements must meet in order to mitigate spinal, muscular, joint, or other physiological discomfort experienced during or after sleep.

In a preferred embodiment, the method includes the step of using a control interface 405 to control the raising and lowering of the support surface 125, and process electronic data received from the one or more measurement devices 120. Using the control interface 405, a user is able to operate the system 100 and test the effects of a support surface 125 on the spinal profile of a manikin 105. The control interface 405 may house electronics and processing equipment configured to calibrate the one or more measurement devices 102. The method may also include the step of using the control interface 405 to process, display, and output data recorded, indicative of changes in the one or more measurement points. The person skilled in the art will understand that the control interface 405 may be a computing device attached to the suspension frame 115 or alternatively located separately according to operator convenience and usability.

Figure 5:
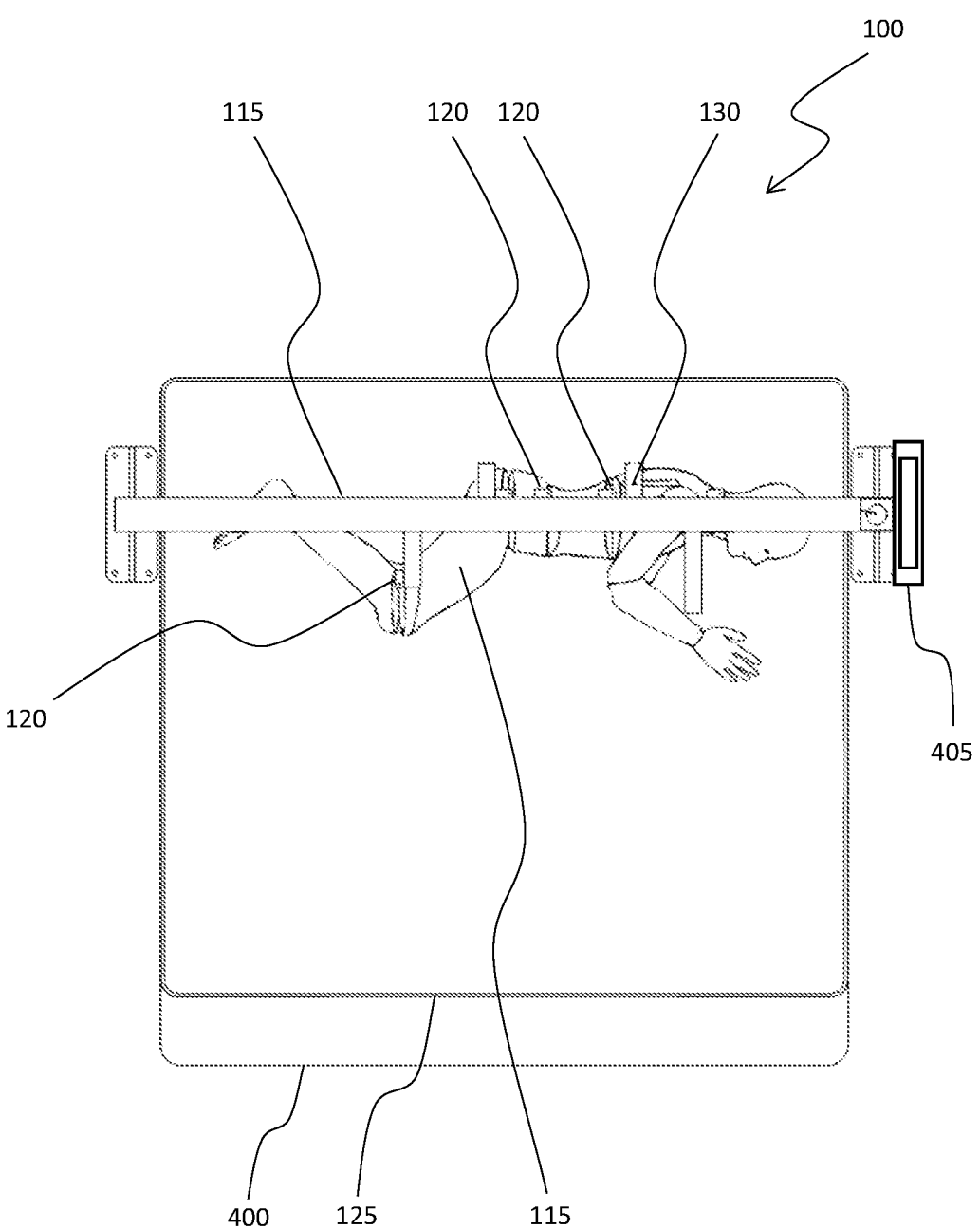
FIG. 5 is a top view of the method of FIG. 1.

FIG. 5 is a top view of the system of FIG. 1, showing a manikin 105 in the lateral position. In a preferred embodiment, the method includes the step of selecting an anatomically accurate human-form manikin sized to realistically represent a human being. Accordingly, the method may include sizing and weighting the manikin 105 according to a 99$^{th}$ percentile male, or sizing and weighting the manikin 105 according to a 1st percentile female. Optionally, the method may include sizing and weighting the manikin 105 according to a size and weight ranging between the 99$^{th}$ percentile male and the 1st percentile female. As an example, the person skilled in the art would understand that according to ergonomic studies in relation to the physical metrics of man and woman, a 95$^{th}$ percentile male measures 188 cm in height and 124 kg in weight, and a 5$^{th}$ percentile female measures 150 cm in height and 50 kg in weight. By incorporating the step of sizing and weighting the manikin 105 according to ergonomic studies, the method allows testing data of each support surface 125 to represent a wide demographic coverage, providing anthropometric data for people of different sizes, relevant to a broad spectrum of the human population.

In a preferred embodiment, a set of acceptable limits for assessing the changes in spinal and/or skeletal angles of the manikin profile for each manikin 105 is established. This allows the control interface 405 to determine how much spinal and/or skeletal profile deviation is caused by a particular support surface 105, and whether the deviations exceed acceptable limits. As mentioned, these acceptable limits may be established by medical research or medical professionals.

FIG. 6 is a flowchart illustrating a method of use for the system of FIG. 1. A flow chart for a test cycle 600 outlines the steps of a preferred method for measuring the spinal and/or skeletal angles of the manikin 105. After setting up the system 100, including the manikin 105, suspension frame 115, and measurement devices 120, a selected support surface 125 is elected for testing and placed on the support base 400 at step 605. At step 610, the support surface 125 and support base 400 is raised until the support surface 125 is close to touching the manikin 105. In a preferred embodiment, the testing sequence of the test cycle 600 may be controlled by the control interface 405.

At step 615, with the support surface 125 close to the manikin 105, but not yet touching, the measuring devices 120 and manikin 105 can be fine calibrated or adjusted so that the passively suspended manikin 105 is in a neutral profile, supine or lateral, and all the measuring devices 120 are zeroed. This allows a baseline from which the testing data can be modelled.

At step 620, the support surface 125 is lifted and used to support the full weight of the manikin 125. Optionally, the support surface 125 may be raised according to a predetermined vertical distance. Preferably, the support surface 125 initially rises and stops after a pre-set vertical distance of between 100 mm and 300 mm. Further preferably, the support surface 125 initially rises and stops after a pre-set vertical distance of between 175 and 200 mm. The person skilled in the art will understand that this initial raising of the support surface 125 is sufficient to take up the full weight of the manikin 105 from the cords 200.

At step 625, the manikin 105 is given time to settle into the support surface 125 and the measuring devices 120 are allowed to achieve a steady state. The person skilled in the art will understand that the manikin 105 may gradually settle over time, depending on the firmness of the support surface 125 or mattress. At step 630, the system 100 is evaluated to determine if the weight of the manikin 105 is fully supported by the support surface 125, or if, after settling, the cords 200 have taken up some of the weight of the manikin 105 once more. If the weight of the manikin 105 is not fully supported by the support surface 125, the support surface may be raised again at step 635. Optionally, the manikin 105 may be raised incrementally over time, allowing the manikin 105 to settle, until the full weight of the manikin 105 is taken up by the support surface 125.

At step 640, once the full weight of the manikin 105 is taken up by the support surface 125, the displacement values can be recorded and the spinal and/or skeletal angles and profile of the manikin 105 is calculated. This allows the control interface 405 to generate data indicating the deviation of the spinal and/or skeletal profile, returning a result set in either numerical and/or diagrammatic representations of the manikin profile. Preferably, the displacement values recorded at step 640 include at least data gathered from measuring points corresponding to the neck, sternum, lumbar, hip, knee, and baseline surface height. The person skilled in the art will understand that if the manikin 105 is tested in the supine position, additional measurement points may be required. For example, two measurement points are required for the hip, as well as one measurement point for each knee.

At step 645, the support base 400 is lowered to the start position, and the support surface 125 is allowed to recover. The test cycle 600 may conclude, or the support surface 125 may be raised again and the test repeated in step 650. If the test is repeated for the same support surface 125 and multiple repeat cycles are undertaken, an average of the logged data or recorded values may be generated, to establish an average manikin profile in response to a particular support surface 125.

The method using the system 100 therefore addresses at least some of the aforementioned problems, providing an accurate method to replicate and measure human physiology, assessing the effect of different surfaces on specific skeletal and spinal and/or skeletal angles. As a method to measure a manikin 105 in the supine or lateral side sleeping position, in depth study and data collection of supine or lateral spinal and/or skeletal profile changes can be effectively conducted and observed. In combination with medical advice and collaboration with medical professionals, impact and effects of different support surfaces 125 can be assessed and parameters of the support surfaces 125 adjusted accordingly to improve the physiological comfort and wellbeing of human users.

In this patent specification, adjectives such as first and second, left and right, top and bottom, up and down, upper and lower, rear, front and side, etc., are used solely to define one element or method step from another element or method step without necessarily requiring a specific relative position or sequence that is described by the adjectives. Words such as "comprises" or "includes" are not used to define an exclusive set of elements or method steps. Rather, such words merely define a minimum set of elements or method steps included in a particular embodiment of the present invention.

The above description of various embodiments of the present invention is provided for purposes of description to one of ordinary skill in the related art. It is not intended to be exhaustive or to limit the invention to a single disclosed embodiment. Numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the scope of the above described invention, which is determined by the following claims.

The invention claimed is:

1. A method for measuring a profile of a manikin, the method comprising the steps of:
    suspending the manikin by a suspension frame, the manikin comprising one or more articulating joints defining a manikin profile, the articulating joints including articulating hip joints that hinge sideways and rotate, enabling a knee of the manikin to rest on a support surface when the manikin is in a lateral position;
    wherein the manikin defines a suspended configuration when suspended by the suspension frame;
    adjusting resistance or the limit of angle of articulation in the articulating joints;
    connecting one or more measuring devices to the manikin at one or more measuring points;

raising the support surface to meet the manikin;
    supporting the manikin by the support surface, wherein the manikin defines a supported configuration when supported by the support surface; and
    measuring by the one or more measuring devices, differences in angles of the manikin profile between the suspended configuration of the manikin and the supported configuration of the manikin.

2. The method of claim 1, further comprising the step of positioning the manikin in a supine position or a lateral position.

3. The method of claim 1, wherein the manikin profile in the suspended configuration is sagittal to the manikin, and the manikin profile is deviated in the supported configuration.

4. The method of claim 1, further comprising the step of suspending the manikin on the suspension frame via a plurality of cords.

5. The method of claim 4, wherein the plurality of cords are tight when in the suspended configuration, and the plurality of cords are slack when in the supported configuration.

6. The method of claim 1, wherein the full weight of the manikin is on the suspension frame when in the suspended configuration, and the full weight of the manikin is on the support surface when in the supported configuration.

7. The method of claim 1, wherein the support surface is a mattress.

8. The method of claim 1, further including the step of supporting a head of the manikin by a counterweight and maintaining the head in a neutral position along the manikin profile.

9. The method of claim 1, further including the step of attaching the one or more measuring points along the manikin profile.

10. The method of claim 1, further including the step of mounting the measuring devices on the suspension frame and connecting the measuring devices to the manikin at the one or more measuring points, wherein the measuring devices are electronic devices.

11. The method of claim 1, further including the step of calibrating the measuring devices.

12. The method of claim 1, further including the step of controlling raising and lowering of the support surface via a control interface.

13. The method of claim 12, further including the step of the control interface processing, displaying, and/or outputting data from the one or more measurement devices.

14. The method of claim 1, further including the step of sizing the manikin according to a size between a 99th percentile male and a 1st percentile female.

15. The method of claim 1, further including the step of weighting the manikin according to a weight between a 99th percentile male and a 1st percentile female.

16. The method of claim 1, wherein differences in angles measured by the one or more measuring devices is calculated from differences in vertical height.

17. The method of claim 1, further including the step of assessing the changes in angles of the manikin profile against a set of acceptable limits.

18. The method of claim 1, further including the step of determining an average of differences in angles of the manikin profile over repeated cycles of the method.

19. The method of claim 1, wherein the resistance and the limit of angle of articulation are adjusted in the articulating hip joints.

20. The method of claim 1, wherein adjusting resistance or the limit of angle of articulation in the articulating joints is imposed to simulate flexibility and movement ranges of the human body.

* * * * *